(12) United States Patent
McGowan et al.

(10) Patent No.: US 10,781,216 B2
(45) Date of Patent: Sep. 22, 2020

(54) PYRROLO [3,2-D]PYRIMIDINE DERIVATIVES FOR THE TREATMENT OF VIRAL INFECTIONS AND OTHER DISEASES

(71) Applicant: JANSSEN SCIENCES IRELAND UNLIMITED COMPANY, County Cork (IE)

(72) Inventors: David Craig McGowan, Brussels (BE); Serge Maria Aloysius Pieters, Hulst (NL); Stefaan Julien Last, Lint (BE); Werner Embrechts, Beerse (BE); Tim Hugo Maria Jonckers, Heist-op-den-Berg (BE); Pierre Jean-Marie Bernard Raboisson, Rosieres (BE)

(73) Assignee: JANSSEN SCIENCES IRELAND UNLIMITED COMPANY, Ringaskiddy, Co Co (IE)

( * ) Notice: Subject to any disclaimer, the term of this patent is extended or adjusted under 35 U.S.C. 154(b) by 0 days.

(21) Appl. No.: 16/441,213

(22) Filed: Jun. 14, 2019

(65) Prior Publication Data

US 2020/0002342 A1    Jan. 2, 2020

Related U.S. Application Data

(63) Continuation of application No. 14/392,214, filed as application No. PCT/EP2014/063467 on Jun. 26, 2014, now Pat. No. 10,385,054.

(30) Foreign Application Priority Data

Jun. 27, 2013 (EP) .................................. 13174108

(51) Int. Cl.
C07D 487/04 (2006.01)

(52) U.S. Cl.
CPC ................. *C07D 487/04* (2013.01)

(58) Field of Classification Search
None
See application file for complete search history.

(56) References Cited

U.S. PATENT DOCUMENTS

| | | |
|---|---|---|
| 6,028,076 A | 2/2000 | Hirota et al. |
| 6,329,381 B1 | 12/2001 | Kurimoto et al. |
| 6,376,501 B1 | 4/2002 | Isobe et al. |
| 6,458,798 B1 | 10/2002 | Fujita et al. |
| 6,503,908 B1 | 1/2003 | Maw |
| 6,583,148 B1 | 6/2003 | Kelley et al. |
| 6,951,866 B2 | 10/2005 | Fujita et al. |
| 7,030,118 B2 | 4/2006 | Lombardo et al. |
| 7,091,232 B2 | 8/2006 | Chow et al. |
| 7,498,409 B2 | 3/2009 | Vlach et al. |
| 7,524,852 B2 | 4/2009 | Arai et al. |
| 7,531,547 B2 | 5/2009 | Dillon et al. |
| 7,754,728 B2 | 7/2010 | Isobe et al. |
| 7,923,554 B2 | 4/2011 | Hoornaert et al. |
| 8,012,964 B2 | 9/2011 | Kurimoto et al. |
| 8,022,077 B2 | 9/2011 | Simmen et al. |
| 8,455,458 B2 | 6/2013 | Marcum et al. |
| 8,486,952 B2 | 7/2013 | Boy et al. |
| 8,637,525 B2 | 1/2014 | Boy et al. |
| 8,916,575 B2 | 12/2014 | McGowan et al. |
| 9,133,192 B2 | 9/2015 | McGowan et al. |
| 9,284,304 B2 | 3/2016 | McGowan et al. |
| 9,365,571 B2 | 6/2016 | McGowan et al. |
| 9,376,448 B2 | 6/2016 | Charifson et al. |
| 9,416,114 B2 | 8/2016 | Gembus et al. |
| 9,422,250 B2 | 8/2016 | McGowan |
| 9,499,549 B2 | 11/2016 | McGowan et al. |
| 9,556,176 B2 | 1/2017 | Bonfanti et al. |
| 9,556,199 B2 | 1/2017 | McGowan et al. |
| 9,598,378 B2 | 3/2017 | McGowan et al. |
| 9,663,474 B2 | 5/2017 | Last et al. |
| 9,878,996 B2 | 1/2018 | Silverman et al. |
| 2005/0054590 A1 | 3/2005 | Averett |
| 2006/0258682 A1 | 11/2006 | Liao et al. |
| 2007/0225303 A1 | 9/2007 | Ogita et al. |
| 2009/0285782 A1 | 11/2009 | Gao et al. |
| 2010/0143299 A1 | 6/2010 | Gao et al. |
| 2014/0148433 A1 | 5/2014 | Follmann et al. |
| 2015/0274676 A1 | 10/2015 | McGowan et al. |
| 2015/0299221 A1 | 10/2015 | Bonfanti et al. |
| 2016/0304531 A1 | 10/2016 | Bonfanti et al. |

FOREIGN PATENT DOCUMENTS

| | | |
|---|---|---|
| CN | 101784548 A | 7/2010 |
| EP | 0882727 | 12/1998 |
| EP | 0899263 A3 | 3/1999 |
| EP | 1552842 A1 | 6/2003 |

(Continued)

OTHER PUBLICATIONS

Isobe, et al., "Synthesis and Biological Evaluation of Novel 9-Sub-stituted-8-Hydroxyadenine Derivatives as Potent Inferferon Inducers", J. Med. Chem., vol. 49; pp. 2088-2095 (2006).

Jurk, et al., "Human TLR7 or TLR8 Independently Confer Responsiveness to the Antiviral Compound R-848", Nature Immunology, Jun. 2002, pp. 499, vol. 3 (6).

Kurimoto, et al., "Synthesis and Evaluation of 2-Substituted 8-Hydroxyadenines as Potent Interferon Inducers with Improved Oral Bioavailabilities", Bioorganic & Medicinal Chemistry, vol. 12; pp. 1091-1099 (2004).

Lee, et al., "Activation of Anti-Hepatitis C Virus Responses via Toll-Like Receptor 7", PNAS, vol. 3 (6); pp. 1828-1833 (Feb. 7, 2006).

(Continued)

*Primary Examiner* — Kortney L. Klinkel
*Assistant Examiner* — Tori Strong
(74) *Attorney, Agent, or Firm* — Brian C. Trinque; Lathrop GPM LLP

(57) ABSTRACT

This invention concerns pyrrolo[3,2-d]pyrimidine derivatives, processes for their preparation, pharmaceutical compositions, and their use in treatment and/or therapy of diseases.

17 Claims, No Drawings
Specification includes a Sequence Listing.

(56) References Cited

FOREIGN PATENT DOCUMENTS

| | | |
|---|---|---|
| EP | 1110951 A1 | 6/2006 |
| EP | 1939198 A1 | 7/2008 |
| EP | 1970373 A1 | 9/2008 |
| EP | 2133353 A1 | 12/2009 |
| EP | 2138497 A1 | 12/2009 |
| JP | 64063582 | 3/1989 |
| JP | 2000053653 | 2/2000 |
| JP | 2000053654 | 2/2000 |
| JP | 2008222557 A | 9/2008 |
| JP | 2009528989 A | 8/2009 |
| JP | 2010522151 A | 7/2010 |
| JP | 2010532353 A | 10/2010 |
| WO | 199801448 A1 | 1/1998 |
| WO | 199808847 A1 | 3/1998 |
| WO | 199814448 A1 | 4/1998 |
| WO | 199850370 A1 | 11/1998 |
| WO | 199928321 A1 | 6/1999 |
| WO | 199932122 A1 | 7/1999 |
| WO | 199940091 A1 | 8/1999 |
| WO | 199941253 A1 | 8/1999 |
| WO | 200006577 A1 | 2/2000 |
| WO | 2000061562 A1 | 10/2000 |
| WO | 2002087513 A2 | 11/2002 |
| WO | 2002088080 A2 | 11/2002 |
| WO | 2003055890 A1 | 7/2003 |
| WO | 2006117670 A1 | 11/2003 |
| WO | 2005007672 A2 | 1/2005 |
| WO | 2005092892 A1 | 10/2005 |
| WO | 2006015985 A1 | 2/2006 |
| WO | 2006050843 A1 | 5/2006 |
| WO | 2007034881 A1 | 3/2007 |
| WO | 2007056208 A1 | 5/2007 |
| WO | 2007063934 A1 | 6/2007 |
| WO | 2007084413 A2 | 7/2007 |
| WO | 2007093901 A1 | 8/2007 |
| WO | 2008009078 A2 | 1/2008 |
| WO | 2008073785 A2 | 6/2008 |
| WO | 2008075103 A1 | 6/2008 |
| WO | 2008114008 A1 | 9/2008 |
| WO | 2008114817 A1 | 9/2008 |
| WO | 2008114819 A1 | 9/2008 |
| WO | 2008115319 A2 | 9/2008 |
| WO | 2008147697 A1 | 12/2008 |
| WO | 2009005687 A1 | 1/2009 |
| WO | 2009023179 A2 | 2/2009 |
| WO | 2009030998 A1 | 3/2009 |
| WO | 2009067081 A1 | 5/2009 |
| WO | 2009080836 A2 | 7/2009 |
| WO | 2009099650 A2 | 8/2009 |
| WO | 2009032668 A3 | 9/2009 |
| WO | 2009134624 A1 | 11/2009 |
| WO | 2009157560 A1 | 12/2009 |
| WO | 2010006025 A1 | 1/2010 |
| WO | 2010007116 A3 | 1/2010 |
| WO | 2010133885 A1 | 11/2010 |
| WO | 2011049825 A1 | 4/2011 |
| WO | 2011049987 | 4/2011 |
| WO | 2011062253 A1 | 5/2011 |
| WO | 2011062372 A3 | 5/2011 |
| WO | 2012066335 A1 | 5/2012 |
| WO | 2012067269 A1 | 10/2012 |
| WO | 2012136834 A1 | 10/2012 |
| WO | 2012156498 A1 | 11/2012 |
| WO | 2013068438 A1 | 5/2013 |
| WO | 2013117615 A1 | 8/2013 |
| WO | 2014053595 A1 | 4/2014 |

OTHER PUBLICATIONS

Roethle, et al., "Identification and Optimization of Pteridinone Toll-Like Receptor 7 (TLR7) Agonists for the Oral Treatment of Viral Hepatitis", Journal of Medicinal Chemistry, vol. 56; pp. 7324-73333 (2013).

Baraldi, et al., "New Strategies for the Synthesis of A3 Adenosine Receptor Antagonists", Bioorganic & Medicinal Chemistry, vol. 11: pp. 4161-4169 (2003).

Barker, et al., "A Rapid Conversion of 3-Oxothiolanes into 3-Aminothiophenes", Synthetic Communications, vol. 32(16): pp. 2565-2568 (2002).

Bell, et al., "Chemistry of 5-Pyrimidinecarboxaldehydes", Journal of Heterocyclic Chemistry, vol. 29: pp. 41-44 (Jan.-Feb. 1983).

Bennet, et al. (Editor), "Part XIV Oncology", Cecil Textbook of Medicine. vol. 1, 20th Edition: pp. 1004-1010 (1996).

Bizanek, et al., Isolation and Structure of an Intrastrand Cross-Link Adduct of Mitomycin C nd DNA, Biochemistry, 1992, pp. 3084-3091, vol. 31.

Bruns, et al, "Solubilities of Adenosine Antagonists Determined by Radioreceptor Assay", Journal of Pharmacy and Pharmacology, vol. 41: pp. 590-594 (1989).

De Clercq, et al., "(S)-9-(2,3-Dihydroxypropyl)adenine: An Aliphatic Nucleoside Analaog with Broad-Spectrum r-.Antiviral Activity", Science, 1978, pp. 563-565, vol. 200.

De Nardo, "Toll-Like Receptors: Activation, Signalling and Transcriptional Modulation", Cytokine, 2015, pp. 181-189, vol. 74.

Dermer. "Another Anniversary for the War on Cancer", Bio/Technology, vol. 12: pp. 320 (Mar. 1994).

Douglas, Jr., "Introduction of Viral Diseases", Cecil Textbook of Medicine, 2oth Edition, vol. 2: pp. 1973-42 (1996).

Freshney, et al., Culture of Animal Cells, Manual of Basic Technique, 1983, pp. 1-6, Chapter 1.

Fried, et al., "Peginterferon Alfa-2a Plus Ribavirin for Chronic Hepatitis C Virus Infection", New England Journal of Medicine, Sep. 26, 2002, pp. 975-985, vol. 347 (13).

Grimm, et al., "Toll-like receptor (TLR) 7 and TLR8 expression on CD133+ cells in colorectal cancer points to a specific rold for inflammation inducted TLRs in tumourigenesis and tumour progression", European Journal of Cancer, 2010, pp. 2849-2857, vol. 46.

Hackam, et al, "Translation of Research Evidence From animals to Humans", JAMA, vol. 296 (14): pp. 1731-1732 (2006).

Hood, et al, "Immunoprofiling toll-like receptor ligands Comparison of Immunostimulatory and proinflammatory profiles in ex vivo human blood models", Human Vaccines, vol. 6(4): pp. 322-335 (Apr. 2010).

Horscroft, et al, "Antiviral applications of toll-like receptor agonists", J. Antimicrob. Chemother., pp. 1-13 (Jan. 18, 2016).

Isobe, et al, "Synthesis and Structure-Activity Relationships of 2-Substituted-8-hydroxyadenine Derivatives as Orally Available Interferon Inducers without Emetic Side Effects", Bioorganic & Medicinal Chemistry, vol. 11: pp. 3641-3647, (2003).

Jiang, et al, "Synthesis of 4-chlorothieno[3,2-d)pyrimidine", Chemical Industry and Engineering Progress, vol. 30: pp. 2532-2535, (2011). [With English Abstract].

Jordan, "Tamoxifen: A Most Unlikely Pioneering Medicine", Nature Reviews, vol. 2: pp. 205-213, Mar. 2003).

Kanzler, et al, "Therapeutic Targeting of Innate Immunity with Toll-Like Receptor Agonists and Antagonists", Nature Medicine, vol. 13(5): pp. 552-559 (May 2007).

Krieger, et al, Enhancement of Hepatitis C Virus RNA Replication by Cell Culture, Journal of Virology, May 1, 2001, 4614-1624, 75-10, DE.

Kurimoto, et al, "Synthesis and Structure—Activity Relationships of 2-Amino-8-hydroxyadenines as Orally Active Interferon Inducing Agents", Bioorganic & Medicinal Chemistry, vol. 11: pp. 5501-5508 (2003).

Liu, et al, "Synthesis and Biological Activity of 3-and 5-Amino Derivatives of Pyridine-2Carboxaldehyde Thiosemicarbazone", J_ Med. Chem, Vo. 39: pp. 2586-2593 (1996).

Lohmann et al, Viral and Cellular Determinants of Hepatitis C Virus RNA Replication in Cell Culture, Journal of Virology, Mar. 2003, pp. 3007-3019, vol. 77, No. 5.

Lohmann, et al., Replication of Subgenomic Hepatitis C Virus RNAs in a Hepatoma Cell Line, Science, 1999, pp. 110-113, vol. 285.

(56) References Cited

OTHER PUBLICATIONS

Makkouk et al., "The potential use of Toll-Like Receptors (TLR) agonistd and antagonists as prophylactic and/or therapeutic agents", Immunopharmacology and Immunotoxicology, vol. 31(3): pp. 331-338 (2009).
McGowan et al., "Novel Pyrimidine Toll-Like Receptor 7 and 8 Dual Agonists to Treat Hepatitis B Virus", Journal of Medicinal Chemistry, 2016, pp. 7936-7949, vol. 59 No. 17.
Mesguiche, et al., "4-Alkoxy-2,6-diaminopyrimidine Derivatives: Inhibitors of Cyclin Dependent Kinases 1 and 2", Bioorganic & Medicinal Chemistry Letters, vol. 13: pp. 217-222 (2003).
Moreau, et al., "Synthesis of cyclic adenosine 5'-diphosphate ribose analogues: a C2' endo/syn "southern" ribose conformation underlies activity at the sea urchin cADPR receptor", Organic & Biomolecular Chemistry, vol. 9: pp. 278-290 (2011).
Musmuca, et al, "Small-Molecule interferon Inducers. Toward the Comprehension of the Molecular Determinants through Ligand-Based Approaches", J. Chem. Inf. Model., vol. 49: pp. 1777-1786 (2009).
O'Hara, et al., "Regioselective Synthesis of Imidazo[4,5-g]quinazoline Quinone Nucleosides and Quinazoline Amino Nucleosides. Studies of their Xanthine Oxidase and Purine Nucleoside Phosphorylase Substrate Activity", J. Org. Chem. vol. 56., pp. 776-785 (1991).
Ohto, et al., "Structure and Function of Toll-Like Receptor 8", Microbes and Infections, vol. 16: pp. 273-282 (2014).
Organic Syntheses Collective, "3-Methylcoumarone", Organic Syntheses Collective, 1963, pp. 43-46, vol. 4.
Thomas, et al., "Investigating Toll-Like Receptor Agonists for Potential to Treat Hepatitis C Virus Infection", Antimicrobial Agents and Chemotherapy, vol. 51(8): pp. 2969-2978 (Aug. 2007).
Tomonori, et al., "Ti-Crossed-Claisen Condensation between Carboxylic Ester and Acid Chlorides or Acids: A Highly Selective and General Method for the Preparation of Various-Keto Esters", Journal of the American Chemical Society, vol. 127:pp. 2854-2855 (2005).
Ulrich, et al, "Crystallization", Kirk-othmer Encyclopedia of Chemical Technology, Chapter 4: pp. 1-63, (Aug. 16 2002).
Vedantham, et al., "Mechanism of Interferon Action in Hairy Cell Leukemia: A Model of Effective Cancer Biotherapy", Cancer Research, vol. 52: pp. 1056-1066 (Mar. 1, 1992).
Vippagunta, et al., "Crystalline Solids", Advance Drug Delivery Reviews, vol. 48: pp. 3-26 (2001).
Warshakoon, et al., "Potential Adjuvantic Properties of Innate Immune Stimuli", Human Vaccines, vol. 5(6): pp. 381-394 (Jun. 2009).
Wermuth, "Molecular Variations Based on Isosteric Replacements", The Practice of Medicinal Chemistry, 1996, pp. 203-237, Ch. 13.
Wolff, et al, Burger's Medicinal Chemistry and Drug Discovery,—, 1994, pp. 975-977, 5th Edition, vol. 1.
Yin, et al., "Synthesis of 2,4-Diaminoquinazolines and Tricyclic Quinazolines by Cascade Reductive Cyclization of Methyl N-Cyano-2-nitrobenzimidates", J. Org. Chem., vol. 77: pp. 2649-2658 (2012).
Yu et al, "Toll-Like Receptor 7 Agonists: Chemical Feature Based", PLOS ONE, vol. 8 (3): pp. 1-11 e56514, (Mar. 20, 2013).
Yu, et al., "Dual Character of Toll-Like Receptor Signaling: Pro-Tumorigenic Effects and Anti-Tumor Functions", Eliochimica et Biophysica Acta, vol. 1835: pp. 144-154 (2013).
U.S. Appl. No. 14/434,021 / US 2015-0239892 A1/ U.S. Pat. No. 9,499,549, filed Apr. 7, 2015 / Aug. 27, 2015 / Nov. 22, 2016, David Craig McGowan.
U.S. Appl. No. 15/333,947 / US2017-0044169A1/ U.S. Pat. No. 10,259,814, filed Oct. 25, 2016 / Feb. 16, 2017 / Apr. 16, 2019, David Craig McGowan.
U.S. Appl. No. 16/382,727, filed Apr. 12, 2019, David Craig McGowan.
U.S. Appl. No. 14/392,214 / US2016-0168150A1 / U.S. Pat. No. 10,385,054, filed Jun. 26, 2014 / Jun. 16, 2016 / Aug. 20, 2019, David Craig McGowan.
Zhao, et al., "Toll-Like Receptors and Prostate Cancer", Frontiers in Immunology, vol. 5 (Article 352): pp. 1-7 (Jul. 2014).
Huddleston et al "A Convenient Synthesis of 2-Substituted 3-Hydroxy and 3-Amino-Thiophens From Derivatives of 2-Chloroacrylic Acid" Synthetic Communications, 1979, vol. 9(8) pp. 731-734.
Abdillahi et al "Synthesis of a Novel Series of Thieno[3,2-D]Pyrimidin-4-(3H)-Ones" Synthesis 2010 vol. 9 pp. 1428-1430 2010.
Banker (Editor), "Prodrugs", Modem Pharmaceutics, Third Edition: pp. 596 (1976).
Brittain, et al., "Effects of Pharmaceutical Processing on Drug Polymorphs and Solvates", polymorphism in Pharmaceutical Solids, 1999, pp. 331-360, Chapter 8.
Chawla, et al., "Challenges in Polymorphism of Pharmaceuticals", Current Research & Information on Pharmaceutical Sciences, vol. 5(1): pp. 9-12 (Jan.-Mar. 2004).
Newman, et al., "Solid-State Analysis of the Active Pharmaceutical Ingredient in Drug Products", Drug Discovery Today, Oct. 19, 2003, pp. 898-905, vol. 8(19).
International Search Report for Corresponding Application No. PCT/EP2012/056388, dated May 31, 2012.
International Search Report for Corresponding Application No. PCT/EP2012/059234, dated Nov. 18, 2013.
International Search Report for Corresponding Application No. EP11166538.6, dated Nov. 22, 2011.
International Search Report for Corresponding Application No. PCT/EP2012/072090, dated Jan. 4, 2013.
International Search Report for Corresponding Application No. PCT/EP2013/052372, dated Apr. 17, 2013.
International Search Report for Corresponding Application No. PCT/EP2013/064763, dated Aug. 3, 2013.
International Search Report for Corresponding Application No. PCT/EP2013/066673, dated Sep. 6, 2013.
International Search Report for Corresponding Application No. PCT/EP2013/070990, dated Jan. 17, 2014.
International Search Report for Corresponding Application No. PCT/EP2013/070488, dated Nov. 14, 2013.
International Search Report for Corresponding Application No. PCT/EP2013/073901, dated Dec. 16, 2013.
International Search Report for Corresponding Application No. PCT/EP2014/053273, dated Mar. 18, 2014.
International Search Report for Corresponding Application No. PCT/EP2014/056270, dated Jul. 21, 2014.
International Search Report for Corresponding Application No. PCT/EP2014/060603, dated Jul. 15, 2014.
International Search Report for Corresponding Application No. PCT/EP2014/066219, dated Nov. 13, 2014.
Akira, S., (Takeda), et al., "Toll-Like Receptors", Annu. Rev. Immunology, vol. 21, pp. 335-376 (2003).
Hoffmann, Jules A., "The Immune Response of *Drosophila*", Nature, vol. 42638 (2003), pp. 33-38.
Ulevitch, Richard J., "Therapeutics Targeting the Innate Immune System", Nature Reviews, vol. 4, pp. 512-520.
International Search Report dated Nov. 3, 2014 for Application No. PCT/EP2014/063467.

PYRROLO [3,2-D]PYRIMIDINE DERIVATIVES FOR THE TREATMENT OF VIRAL INFECTIONS AND OTHER DISEASES

CROSS-REFERENCE TO RELATED APPLICATIONS

This application is a continuation of Ser. No. 14/392,214, filed on Dec. 23, 2015, which is a national stage filing under USC § 371 of international application PCT/EP2014/063467 filed on Jun. 26, 2014, which claims priority to European Patent Application No. 13174108.4 filed Jun. 27, 2013, the complete disclosures of which are hereby incorporated herein by reference for all purposes.

SEQUENCE LISTING

The instant application contains a Sequence Listing which has been submitted electronically in ASCII format and is hereby incorporated by reference in its entirety. Said ASCII copy, created on Jun. 13, 2019, is named 613314-NTT-300USCON-SEQ-LISTING.TXT and is 604 bytes in size.

This invention relates to pyrrolo[3,2-d]pyrimidine derivatives, processes for their preparation, pharmaceutical compositions, and their use in treatment and/or therapy of diseases.

The present invention relates to the use of pyrrolo[3,2-d]pyrimidine derivatives, more specifically to the use of pyrrolo[3,2-d]pyrimidine derivatives in the treatment of viral infections, immune or inflammatory disorders, whereby the modulation, or agonism, of toll-like-receptors (TLRs) is involved. Toll-Like Receptors are primary transmembrane proteins characterized by an extracellular leucine rich domain and a cytoplasmic extension that contains a conserved region. The innate immune system can recognize pathogen-associated molecular patterns via these TLRs expressed on the cell surface of certain types of immune cells. Recognition of foreign pathogens activates the production of cytokines and upregulation of co-stimulatory molecules on phagocytes. This leads to the modulation of T cell behaviour.

A majority of mammalian species have between ten and fifteen types of Toll-like receptors. Thirteen TLRs (named simply TLR1 to TLR13) have been identified in humans and mice together, and equivalent forms of many of these have been found in other mammalian species. However, equivalents of certain TLR found in humans are not present in all mammals. For example, a gene coding for a protein analogous to TLR10 in humans is present in mice, but appears to have been damaged at some point in the past by a retrovirus. On the other hand, mice express TLRs 11, 12, and 13, none of which are represented in humans. Other mammals may express TLRs which are not found in humans. Other non-mammalian species may have TLRs distinct from mammals, as demonstrated by TLR14, which is found in the Takifugu pufferfish. This may complicate the process of using experimental animals as models of human innate immunity.

For reviews on toll-like receptors see the following journal articles. Hoffmann, J. A., Nature, 426, p 33-38, 2003; Akira, S., Takeda, K., and Kaisho, T., Annual Rev. Immunology, 21, p 335-376, 2003; Ulevitch, R. J., Nature Reviews: Immunology, 4, p 512-520, 2004.

Compounds indicating activity on Toll-Like receptors have been previously described such as heterocyclic derivatives in WO2000/006577, adenine derivatives in WO98/01448 and WO99/28321, and pyrimidines in WO2009/067081.

In the treatment of certain viral infections, regular injections of interferon (IFN-alfa) can be administered, as is the case for hepatitis C virus (HCV). Orally available small molecule IFN inducers offer the potential advantages of reduced immunogenicity and convenience of administration. Thus, novel IFN inducers are potentially effective new class of drugs for the treatment of viral infections. For an example in the literature of a small molecule IFN inducer having antiviral effect see De Clercq, E.; Descamps, J.; De Somer, P. Science 1978, 200, 563-565.

Interferon α is also given to patients in combination with other drugs in the treatment of certain types of cancer. TLR 7/8 agonists are also of interest as vaccine adjuvants because of their ability to induce pronounced Th1 response.

However, there exists a strong need for novel Toll-Like receptor modulators having preferred selectivity, and an improved safety profile compared to the compounds of the prior art.

In accordance with the present invention a compound of formula (I) is provided

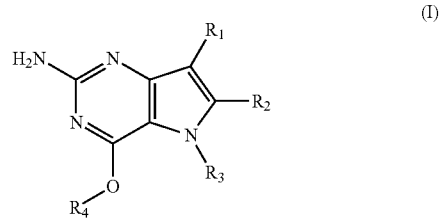

and their pharmaceutically acceptable salt, solvate or polymorph thereof wherein $R_1$ is H, fluorine or methyl;

$R_2$ is H, halogen or $C_{1-3}$ alkyl;

$R_3$ is $C_{1-6}$ alkyl optionally substituted by one or more substituents independently selected from aryloxy, heterocycle, halogen, aryl, alkylamino, dialkylamino, $C_{1-6}$ alkyl, carboxylic acid, carboxylic ester, carboxylic amide, nitrile, or $C_{1-6}$ alkoxy;

or wherein $R_3$ is an alkylaryl optionally substituted by one or more substituents independently selected from halogen, aryloxy, aryl, alkylamino, dialkylamino, $C_{1-6}$ alkyl, carboxylic acid, carboxylic ester, carboxylic amide, sulfonamide, nitrile, or $C_{1-6}$ alkoxy;

$R_4$ is $C_{1-6}$ alkyl optionally substituted by one or more substituents independently selected from hydroxyl, $C_{1-6}$ alkyl, $C_{3-7}$ cycloalkyl, $C_{2-6}$ alkenyl or aryl optionally further substituted by $C_{1-6}$ alkyl, and $C_{3-7}$ cycloalkyl optionally further substituted by $C_{1-6}$ alkyl;

or wherein $R_4$ is an alkylaryl optionally substituted by one or more substituents independently selected from halogen, aryloxy, aryl, alkylamino, dialkylamino, $C_{1-6}$ alkyl, carboxylic acid, carboxylic ester, carboxylic amide, sulfonamide, nitrile, or $C_{1-6}$ alkoxy.

Preferred compounds are those of formula (I) wherein $R_3$ is a $CH_2$-aryl group (substituted or unsubstituted), and $R_1$, $R_2$, and $R_4$ are described as above.

In a second embodiment are the compounds of formula (I) wherein $R_3$ and $R_4$ are both $CH_2$-aryl groups optionally further substituted as described above, and $R_1$, and $R_2$ are as described as above.

Other preferred embodiments are those of formula (I) wherein $R_1$ is fluorine, $R_2$ is hydrogen, and $R_3$ and $R_4$ are described as above.

The most preferred compound is compound of formula (II) having the following chemical structure:

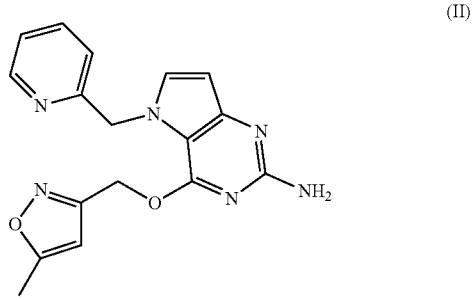 [SMILES: Cc1cc(COc2nc(N)nc3ccn(Cc4ccccn4)c23)no1]

(II)

The compounds of formula (I) and (II) and their pharmaceutically acceptable salt, solvate or polymorph thereof have activity as pharmaceuticals, in particular as modulators of Toll-Like Receptor (especially TLR7) activity.

In a further aspect the present invention provides a pharmaceutical composition comprising a compound of formula (I) or (II) or a pharmaceutically acceptable salt, solvate or polymorph thereof together with one or more pharmaceutically acceptable excipients, diluents or carriers.

Furthermore a compound of formula (I) or (II) or a pharmaceutically acceptable salt, solvate or polymorph thereof according to the current invention, or a pharmaceutical composition comprising said compound of formula (I) or (II) or a pharmaceutically acceptable salt, solvate or polymorph thereof can be used as a medicament.

Another aspect of the invention is that a compound of formula (I) or (II) or a pharmaceutically acceptable salt, solvate or polymorph thereof, or said pharmaceutical composition comprising said compound of formula (I) or (II) or a pharmaceutically acceptable salt, solvate or polymorph thereof can be used accordingly in the treatment of any disorder in which the modulation of TLR7 is involved.

The term "alkyl" refers to a straight-chain or branched-chain saturated aliphatic hydrocarbon containing the specified number of carbon atoms.

The term "halogen" refers to fluorine, chlorine, bromine or iodine.

The term "alkylaryl" refers to a straight-chain or branched-chain saturated aliphatic hydrocarbon containing the specified number of carbon atoms substituted by an aryl wherein "aryl" is defined as below.

The term "alkenyl" refers to an alkyl as defined above consisting of at least two carbon atoms and at least one carbon-carbon double bond.

The term "cycloalkyl" refers to a carbocyclic ring containing the specified number of carbon atoms.

The term "alkoxy" refers to an alkyl (carbon and hydrogen chain) group singular bonded to oxygen like for instance a methoxy group or ethoxy group.

The term "aryl" means an aromatic ring structure optionally comprising one or two heteroatoms selected from N, O and S, in particular from N and O. Said aromatic ring structure may have 5, 6 or 7 ring atoms. In particular, said aromatic ring structure may have 5 or 6 ring atoms.

The term "aryloxy" refers to an aromatic ring structure. Said aromatic group is singularly bonded to oxygen.

The term "heterocycle" refers to molecules that are saturated or partially saturated and include tetrahydrofuran, dioxane or other cyclic ethers. Heterocycles containing nitrogen include, for example azetidine, morpholine, piperidine, piperazine, pyrrolidine, and the like. Other heterocycles include, for example, thiomorpholine, dioxolinyl, and cyclic sulfones.

Pharmaceutically acceptable salts of the compounds of formula (I) and (II) include the acid addition and base salts thereof. Suitable acid addition salts are formed from acids which form non-toxic salts. Suitable base salts are formed from bases which form non-toxic salts.

The compounds of the invention may also exist in unsolvated and solvated forms. The term "solvate" is used herein to describe a molecular complex comprising the compound of the invention and one or more pharmaceutically acceptable solvent molecules, for example, ethanol.

The term "polymorph" refers to the ability of the compound of the invention to exist in more than one form or crystal structure.

The compounds of the present invention may be administered as crystalline or amorphous products. They may be obtained for example as solid plugs, powders, or films by methods such as precipitation, crystallization, freeze drying, spray drying, or evaporative drying. They may be administered alone or in combination with one or more other compounds of the invention or in combination with one or more other drugs. Generally, they will be administered as a formulation in association with one or more pharmaceutically acceptable excipients. The term "excipient" is used herein to describe any ingredient other than the compound(s) of the invention. The choice of excipient depends largely on factors such as the particular mode of administration, the effect of the excipient on solubility and stability, and the nature of the dosage form.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, for example, for oral, rectal, or percutaneous administration. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions, and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. Also included are solid form preparations that can be converted, shortly before use, to liquid forms. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. The compounds of the present invention may also be administered via inhalation or insufflation by means of methods and formulations employed in the art for administration via this way. Thus, in general the compounds of the present invention may be administered to the lungs in the form of a solution, a suspension or a dry powder.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of infectious diseases will be able to determine the effective amount from the test results presented hereinafter. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the individual may be taking, as is well known to those skilled in the art. Furthermore, it is evident that the effective amount may be lowered or increased depending on the response of the treated subject and/or depending on the evaluation of the physician prescribing the compounds of the instant invention. The effective amount ranges mentioned above are therefore only guidelines and are not intended to limit the scope or use of the invention to any extent.

EXPERIMENTAL SECTION

Scheme 1. Overall reaction scheme

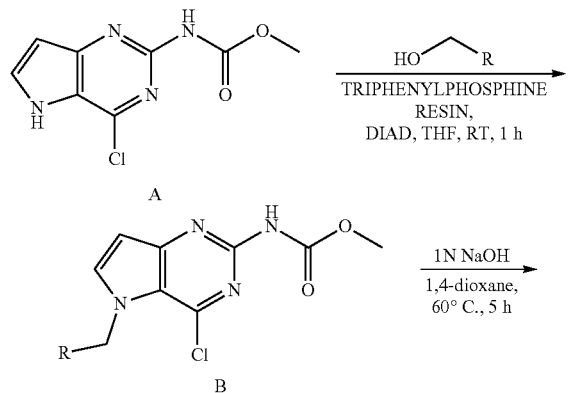

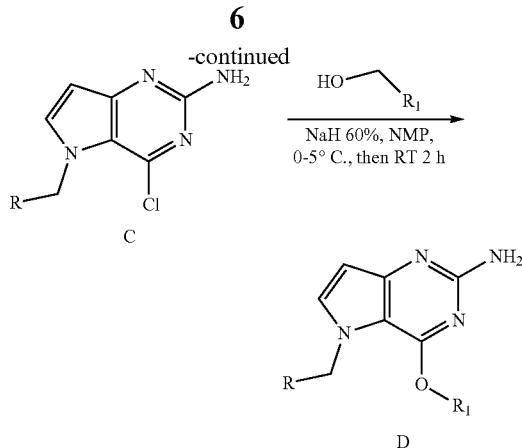

Compounds of type A in scheme 1 can be functionalized with alcohols using Mitsunobu conditions in a polar aprotic solvent, for example THF. The cleavage of the methyl carbamate was performed under basic conditions in 1,4-dioxane to form intermediate C. The displacement of the chlorine in C was performed with an alcohol and a base (e.g. NaH) in a polar aprotic solvent (e.g. NMP) to form compounds of the type D.

Preparation of Intermediate A

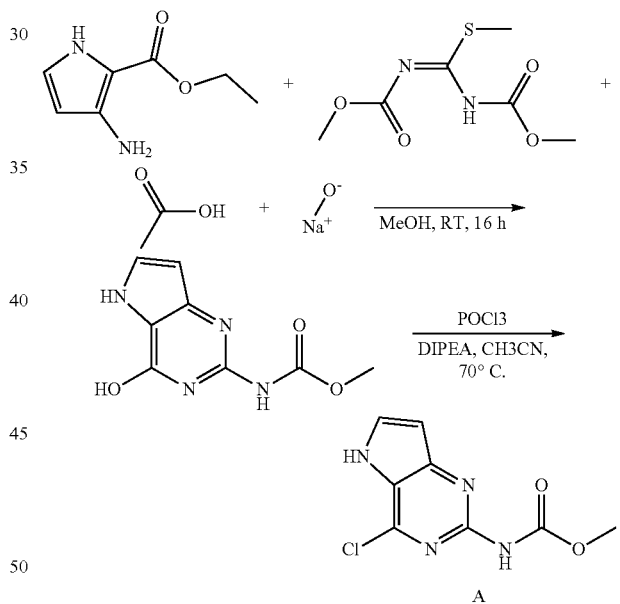

3-Amino-2-ethoxycarbonylpyrrole hydrochloride (25.8 g, 135.3 mmol) was partitioned between dichloromethane and sat. NaHCO$_3$. The organic layer was dried over MgSO$_4$, the solids were removed via filtration, and the solvent of the filtrate evaporated to dryness. The residue was dissolved in methanol (500 mL) together with 1,3-bis(methoxycarbonyl)-2-methyl-2-thiopseudourea (32.1 g, 156 mmol) and acetic acid (39 mL, 677 mmol) and stirred 1 hour at room temperature. A precipitate appeared and stirring was continued overnight. Sodium methoxide (73.1 g, 1353 mmol) was added. An exothermic reaction was observed and the reaction mixture was stirred overnight. The mixture was brought to pH 5 with acetic acid and the precipitate was isolated by filtration, triturated on the filter with water (2×350 mL), acetonitrile (350 mL) and diisopropylether (350 mL). The obtained methyl N-(4-hydroxy-5H-pyrrolo-[3,2-d]pyrimidin-2-yl)carbamate was dried in the oven.

methyl N-(4-hydroxy-5H-pyrrolo[3,2-d]pyrimidin-2-yl)carbamate (25 g, 120 mmol) was dispensed in 350 mL acetonitrile in a 500 mL multi neck flask equipped with an overhead stirrer (300 rpm) at room temperature. POCl$_3$ (22.1 mL, 238.2 mmol) was added and then the reaction mixture was heated to 70° C. while stirring. Diisopropylethylamine (41.4 mL, 240.2 mmol) was added dropwise via a syringe pump at a flow of 0.2 mL/min.

The reaction mixture was cooled to room temperature and poured into a stirred solution of sodium acetate (78.8 g, 961 mmol) in water (500 mL) at 45° C. The organics were evaporated and the remaining liquid was stirred and cooled over an ice bath. The formed solid was isolated by filtration, washed with acetonitrile and triturated with diisopropylether to afford intermediate A, dried under vacuum. LC-MS m/z=227 (M+H)

Preparation of Intermediate B
Method 1.

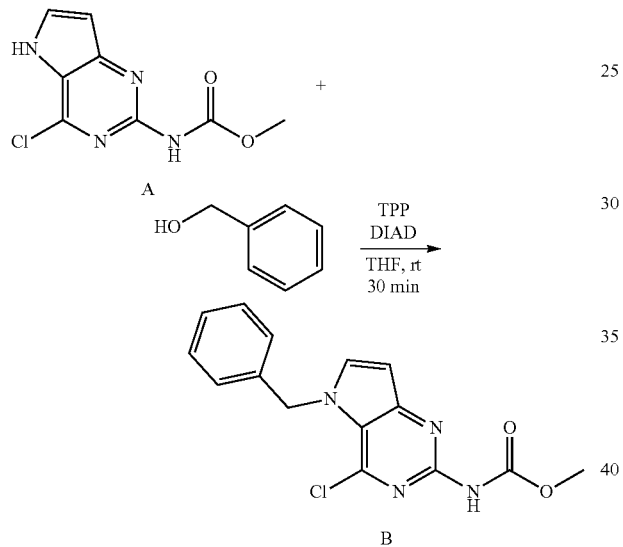

To a suspension of A (500 mg, 2.2 mmol), benzylalcohol (0.28 mL, 2.6 mmol) and triphenylphosphine (0.69 g, 2.6 mmol) in anhydrous THF (15 mL) was added DIAD (0.64 mL, 3.3 mmol) at room temperature. The reaction mixture was stirred at room temperature for 30 minutes. The mixture was concentrated under reduced pressure. The product was purified via silica gel column chromatography using a heptanes to ethyl acetate gradient; 100-0 to 90-10. The product fractions were collected and concentrated under reduced pressure. The product was triturated in diisopropylether, isolated by filtration and dried under vacuum to afford B as a pale yellow solid. LC-MS m/z=317 (M+H)

Method 2 with Resin Bound Triphenylphosphine.

To a suspension of A (700 mg, 3.1 mmol), benzylalcohol (0.39 mL, 3.7 mmol) and triphenylphosphine resin (2.6 g, 7.7 mmol) in anhydrous THF (21 mL) was added DIAD (0.90 mL, 4.6 mmol) at room temperature. The reaction mixture was stirred at room temperature for 1 h. The mixture was filtered over packed decalite and washed with methanol. The filtrate was concentrated in vacuo. The product was triturated in diisopropylether, isolated by filtration and dried under vacuum to afford a pale yellow solid, B. LC-MS m/z=317 (M+H)

Preparation of Intermediate C

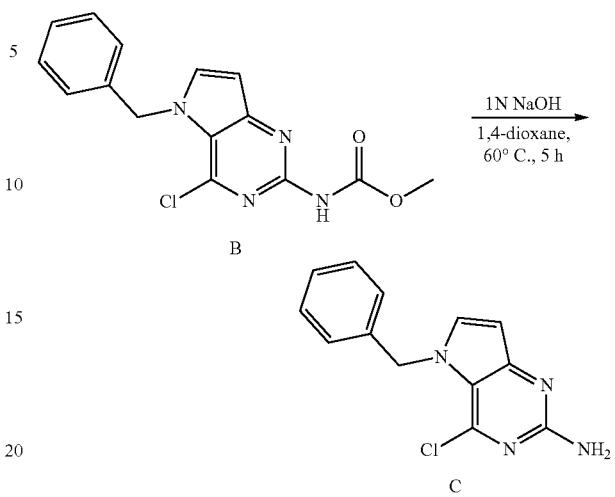

B (738 mg, 2.3 mmol) was dissolved in 1,4-dioxane (11 mL) in a 50 mL glass tube and NaOH (5.6 mL, 1N a.q.) was added. The mixture was heated to 60° C. for 5 h. The mixture was cooled and concentrated in vacuo. The residue was treated with water and the precipitate was isolated by filtration and dried under vacuum to afford C as a solid. The product was used as such in the next step. LC-MS m/z=259 (M+H)

Preparation of 1 and 2
Method 1

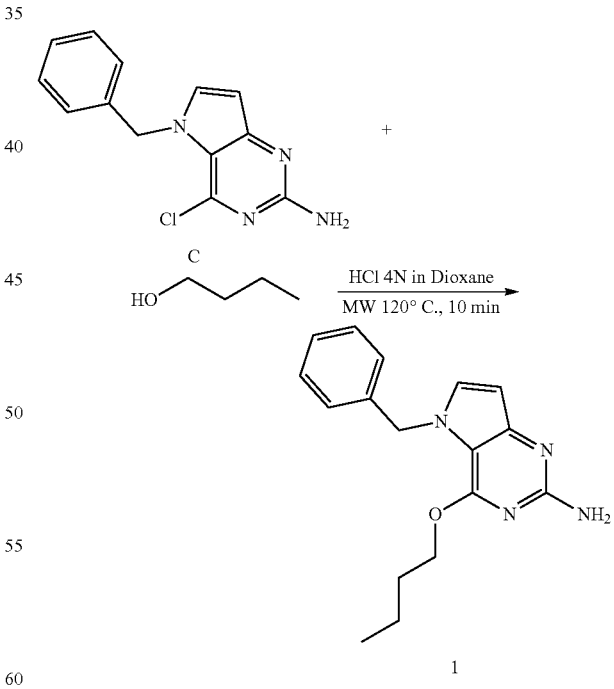

Intermediate C (240 mg, 0.93 mmol), n-butylalcohol (3.2 mL, 35 mmol), and 4N HCl in dioxane (0.46 mL, 1.9 mmol) was placed into a 7 mL microwave vial. The vial was sealed and the mixture was heated in the microwave at 120° C. for 10 minutes. The mixture was cooled and concentrated in vacuo. The residue was neutralized with sat. NaHCO$_3$ solution and extracted with dichloromethane. The organic layer was separated, dried (MgSO₄), the solids were removed by filtration and the filtrate was concentrated under reduced pressure. The product was purified via silica gel column chromatography using a dichloromethane-methanol, 100-0 to 95-5 gradient. The best fractions were collected and concentrated under reduced pressure. The product was triturated in diisopropylether and the solid was isolated by filtration and dried under vacuum to afford 1 as a white solid.

Method 2.

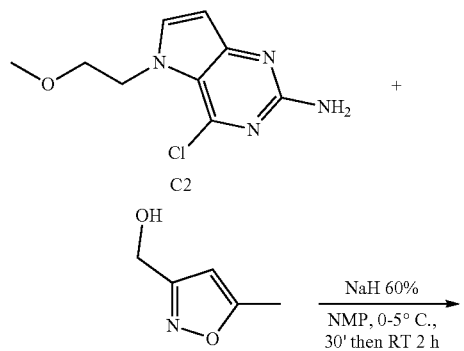

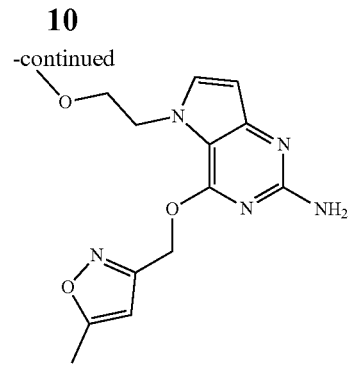

Intermediate $C_2$ (250 mg, 1.1 mmol), and 3-hydroxymethyl-5-methylisoxazole (0.16 mL, 1.65 mmol) were dissolved in NMP (3 mL) in a 7 mL vial. The mixture was cooled on a ice bath and NaH (66 mg, 1.65 mmol, 60% dispersion in mineral oil) was added under $N_2$ and the mixture was stirred at 0-5° C. for 30 minutes and then allowed to warm to room temperature and continued stirring for 2 h. Then crude reaction mixture was purified by preparatory HPLC (Stationary phase: RP Vydac Denali C18 10 μm, 200 g, 5 cm), mobile phase: 0.25% NH₄OAc solution in water, CH₃CN), the desired fractions were collected and concentrated in vacuo. The product was crystallized from CH₃CN, isolated by filtration and dried under vacuum to afford a white solid, 2.

TABLE 1

Compounds of formula (I) and corresponding analytical data. Compounds were prepared according to the methods described in the experimental section.

| # | STRUCTURE | ¹H NMR | LC Method, Rt (min) | LC-MS Mass Found (M + H) |
|---|---|---|---|---|
| 1 | 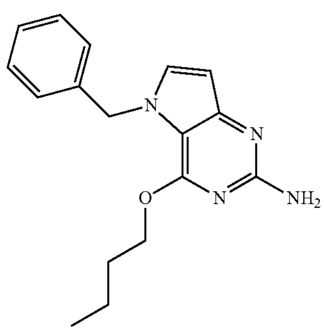 [SMILES: CCCCOc1nc(N)nc2ccn(Cc3ccccc3)c12] | ¹H NMR (400 MHz, DMSO-d₆) δ ppm 0.85 (t, J = 7.37 Hz, 3 H) 1.26 (dq, J = 15.02, 7.39 Hz, 2 H) 1.56-1.63 (m, 2 H) 4.30 (t, J = 6.38 Hz, 2 H) 5.39 (s, 2 H) 5.72 (s, 2 H) 6.08 (d, J = 3.08 Hz, 1 H) 7.03-7.08 (m, 2 H) 7.19-7.25 (m, 1 H) 7.26-7.32 (m, 2 H) 7.48 (d, J = 3.08 Hz, 1 H) | B, 1.98 | 297 |
| 2 | 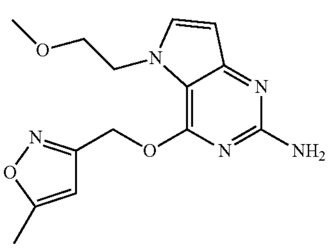 [SMILES: COCCn1ccc2nc(N)nc(OCc3cc(C)on3)c21] | ¹H NMR (400 MHz, DMSO-d₆) δ ppm 2.41 (d, J = 0.66 Hz, 3 H) 3.17 (s, 3 H) 3.57 (t, J = 5.50 Hz, 2 H) 4.29 (t, J = 5.50 Hz, 2 H) 5.50 (s, 2 H) 5.82 (s, 2 H) 6.03 (d, J = 2.86 Hz, 1 H) 6.37 (d, J = 0.88 Hz, 1 H) 7.35 (d, J = 2.86 Hz, 1 H) | A, 0.69 | 304 |

TABLE 1-continued

Compounds of formula (I) and corresponding analytical data. Compounds were prepared according to the methods described in the experimental section.

| # | STRUCTURE | ¹H NMR | LC Method, Rt (min) | LC-MS Mass Found (M + H) |
|---|---|---|---|---|
| 3 | 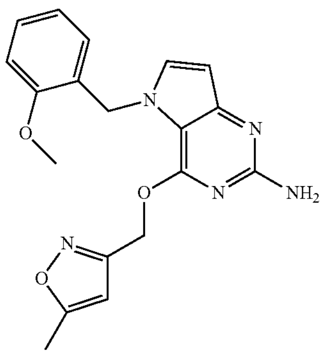 | ¹H NMR (400 MHz, DMSO-d₆) δ ppm 2.33-2.38 (m, 3 H) 3.79 (s, 3 H) 5.34 (s, 2 H) 5.38 (s, 2 H) 5.75 (s, 1 H) 5.86 (s, 2 H) 6.12 (d, J = 3.08 Hz, 1 H) 6.40-6.47 (m, 1 H) 6.78 (td, J = 7.48, 0.66 Hz, 1 H) 7.00 (d, J = 7.92 Hz, 1 H) 7.24 (td, J = 7.80, 1.80 Hz, 1 H) 7.43 (d, J = 2.86 Hz, 1 H) | B, 1.62 | 366 |
| 4 | 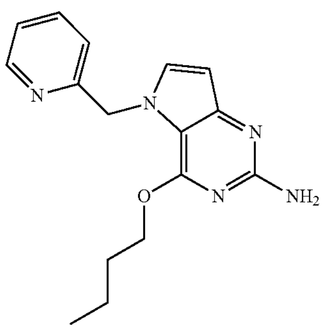 [SMILES: CCCCOc1nc(N)nc2ccn(Cc3ccccn3)c12] | ¹H NMR (400 MHz, DMSO-d₆) δ ppm 0.77 (t, J = 7.4 Hz, 3 H), 1.12 (dq, J = 15.0, 7.4 Hz, 2 H), 1.40-1.50 (m, 2 H), 4.21 (t, J = 6.4 Hz, 2 H), 5.49 (s, 2 H), 5.73 6 (s, 2 H), 6.11 (d, J = 2.9 Hz, 1 H), 6.65 (d, J = 7.9 Hz, 1 H), 7.21-7.28 (m, 1 H), 7.47 (d, J = 3.1 Hz, 1 H), 7.69 (td, J = 7.7, 1.8 Hz, 1 H), 8.47-8.53 (m, 1 H) | A, 0.81 | 298 |
| 5 | 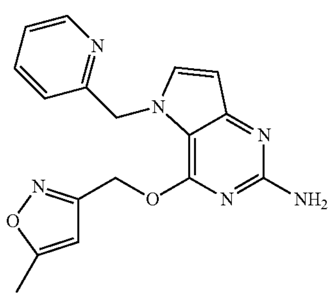 [SMILES: Cc1cc(COc2nc(N)nc3ccn(Cc4ccccn4)c23)no1] | ¹H NMR (400 MHz, DMSO-d₆) δ ppm 2.35 (s, 3 H) 5.37 (s, 2 H) 5.47 (s, 2 H) 5.84-5.90 (m, 3 H) 6.14 (d, J = 2.86 Hz, 1 H) 6.72 (d, J = 7.92 Hz, 1 H) 7.24 (dd, J = 6.93, 4.95 Hz, 1 H) 7.52 (d, J = 3.08 Hz, 1 H) 7.65 (td, J = 7.70, 1.76 Hz, 1 H) 8.47 (d, J = 4.18 Hz, 1 H) | B, 1.29 | 337 |
| 6 | 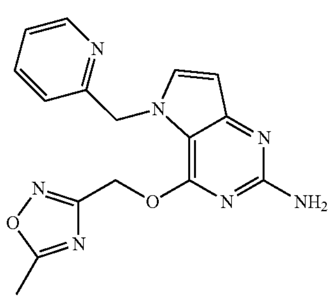 | ¹H NMR (400 MHz, DMSO-d₆) δ ppm 2.57 (s, 3 H) 5.45 (s, 2 H) 5.51 (s, 2 H) 5.85 (s, 2 H) 6.13 (d, J = 2.86 Hz, 1 H) 6.85 (d, J = 7.70 Hz, 1 H) 7.22 (dd, J = 7.04, 5.06 Hz, 1 H) 7.52 (d, J = 3.08 Hz, 1 H) 7.64 (td, J = 7.65, 1.65 Hz, 1 H) 8.43 (d, J = 4.18 Hz, 1 H) | B, 1.14 | 338 |

TABLE 1-continued

Compounds of formula (I) and corresponding analytical data. Compounds were prepared according to the methods described in the experimental section.

| # | STRUCTURE | ¹H NMR | LC Method, Rt (min) | LC-MS Mass Found (M + H) |
|---|---|---|---|---|
| 7 | 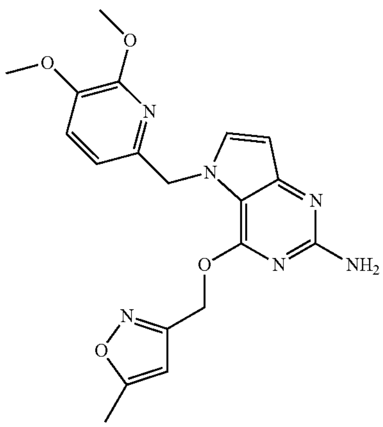 [SMILES: COc1ccc(Cn2ccc3nc(N)nc(OCc4cc(C)on4)c32)nc1OC] | ¹H NMR (400 MHz, DMSO-d₆) δ ppm 2.36 (s, 3 H) 3.74 (s, 3 H) 3.71 (s, 3 H) 5.29 (s, 2 H) 5.40 (s, 2 H) 5.85 (s, 2 H) 5.93 (s, 1 H) 6.12 (d, J = 3.08 Hz, 1 H) 6.29 (d, J = 7.92 Hz, 1 H) 7.11 (d, J = 7.92 Hz, 1 H) 7.50 (d, J = 3.08 Hz, 1 H) | B, 1.45 | 397 |
| 8 | 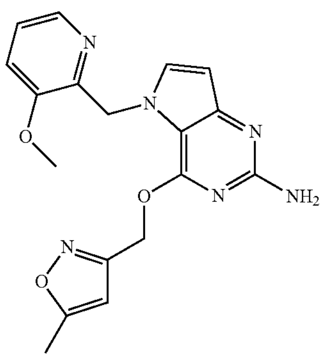 [SMILES: COc1cccnc1Cn1ccc2nc(N)nc(OCc3cc(C)on3)c21] | ¹H NMR (400 MHz, DMSO-d₆) δ ppm 2.36 (s, 3 H) 3.80 (s, 3 H) 5.31 (s, 2 H) 5.48 (s, 2 H) 5.75-5.81 (m, 3 H) 6.07 (d, J = 2.86 Hz, 1 H) 7.25 (dd, J = 8.25, 4.73 Hz, 1 H) 7.36-7.41 (m, 2 H) 7.90 (dd, J = 4.73, 0.99 Hz, 1 H) | A, 0.72 | 367 |
| 9 | 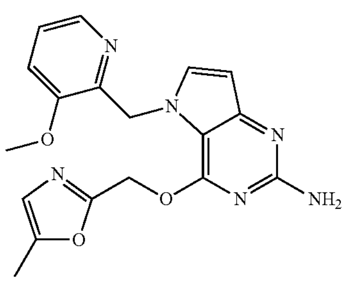 [SMILES: COc1cccnc1Cn1ccc2nc(N)nc(OCc3ncc(C)o3)c21] | ¹H NMR (400 MHz, DMSO-d₆) δ ppm 2.23 (d, J = 1.10 Hz, 3 H) 3.77 (s, 3 H) 5.32 (s, 2 H) 5.45 (s, 2 H) 5.77 (s, 2 H) 6.07 (d, J = 2.86 Hz, 1 H) 6.79 (d, J = 1.10 Hz, 1 H) 7.21 (dd, J = 8.25, 4.73 Hz, 1 H) 7.33 (dd, J = 8.36, 1.32 Hz, 1 H) 7.37 (d, J = 2.86 Hz, 1 H) 7.88 (dd, J = 4.73, 1.21 Hz, 1 H) | B, 1.26 | 367 |
| 10 | 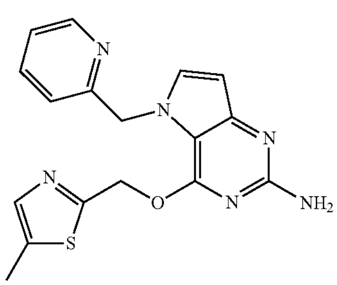 [SMILES: Cc1cnc(COc2nc(N)nc3ccn(Cc4ccccn4)c23)o1] | ¹H NMR (400 MHz, DMSO-d₆) δ ppm 2.34-2.41 (m, 3 H) 5.49 (s, 2 H) 5.58 (s, 2 H) 5.88 (s, 2 H) 6.15 (d, J = 2.86 Hz, 1 H) 6.72 (d, J = 7.92 Hz, 1 H) 7.20-7.25 (m, 1 H) 7.43 (d, J = 1.10 Hz, 1 H) 7.52 (d, J = 2.86 Hz, 1 H) 7.63 (td, J = 7.70, 1.76 Hz, 1 H) 8.46 (dd, J = 4.73, 0.77 Hz, 1 H) | B, 1.28 | 353 |

TABLE 1-continued

Compounds of formula (I) and corresponding analytical data. Compounds were prepared according to the methods described in the experimental section.

| # | STRUCTURE | $^1$H NMR | LC Method, Rt (min) | LC-MS Mass Found (M + H) |
|---|---|---|---|---|
| 11 | (structure: pyridin-2-ylmethyl pyrrolopyrimidine with 5-methyloxazol-2-ylmethoxy and NH$_2$) | $^1$H NMR (400 MHz, DMSO-d$_6$) δ ppm 2.24 (s, 3 H) 5.39 (s, 2 H) 5.43 (s, 2 H) 5.85 (s, 2 H) 6.13 (d, J = 2.86 Hz, 1 H) 6.76 (d, J = 7.70 Hz, 1 H) 6.81 (s, 1 H) 7.21 (dd, J = 6.93, 5.17 Hz, 1 H) 7.52 (d, J = 2.86 Hz, 1 H) 7.62 (td, J = 7.65, 1.43 Hz, 1 H) 8.40 - 8.45 (m, 1 H) | B, 1.18 | 337 |

Analytical Methods.
LCMS General Procedure

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Compounds are described by their experimental retention times (Rt) and ions. If not specified differently in the table of data, the reported molecular ion corresponds to the [M+H]+(protonated molecule) and/or [M−H]− (deprotonated molecule). In case the compound was not directly ionizable the type of adduct is specified (i.e. [M+NH$_4$]+, [M+HCOO]−, etc. . . . ). For molecules with multiple isotopic patterns (Br, Cl . . . ), the reported value is the one obtained for the lowest isotope mass. All results were obtained with experimental uncertainties that are commonly associated with the method used.

Hereinafter, "SQD" means Single Quadrupole Detector, "MSD" Mass Selective Detector, "RT" room temperature, "BEH" bridged ethylsiloxane/silica hybrid, "DAD" Diode Array Detector, "HSS" High Strength silica, "Q-Tof" Quadrupole Time-of-flight mass spectrometers, "CLND", ChemiLuminescent Nitrogen Detector, "ELSD" Evaporative Light Scanning Detector, LC-MS Method codes (Flow expressed in mL/min; column temperature (Col T) in ° C.; Run time in minutes).

Biological Activity of Compounds of Formula (I) and (II)
Description of Biological Assays
Assessment of TLR7 and TLR8 Activity The ability of compounds to activate human TLR7 and/or TLR8 was assessed in a cellular reporter assay using HEK293 cells transiently transfected with a TLR7 or TLR8 expression vector and NFκB-luc reporter construct.

Briefly, HEK293 cells were grown in culture medium (DMEM supplemented with 10% FCS and 2 mM Glutamine). For transfection of cells in 15 cm dishes, cells were detached with Trypsin-EDTA, transfected with a mix of CMV-TLR7 or TLR8 plasmid (1700 ng), NFκB-luc plasmid (850 ng) and a transfection reagent and incubated for 48 h at 37° C. in a humidified 5% CO$_2$ atmosphere. Transfected cells were then washed in PBS, detached with Trypsin-EDTA and resuspended in medium to a density of $1.25 \times 10^5$ cells/mL. Forty microliters of cells were then dispensed into each well in 384-well plates, where 200 nL of compound in 100% DMSO was already present. Following 6 hours incubation at 37° C., 5% CO$_2$, the luciferase activity was determined by adding 15 μL of Steady Lite Plus substrate (Perkin Elmer) to each well and readout performed on a ViewLux ultraHTS microplate imager (Perkin Elmer). Dose response curves were generated from measurements performed in quadruplicates. Lowest effective concentrations (LEC) values, defined as the concentration that induces an effect which is at least two fold above the standard deviation of the assay, were determined for each compound.

Compound toxicity was determined in parallel using a similar dilution series of compound with 40 μL per well of cells transfected with the CMV-TLR7 construct alone ($1.25 \times 10^5$ cells/mL), in 384-well plates. Cell viability was measured after 6 hours incubation at 37° C., 5% CO$_2$ by adding

| Method code | Instrument | Column | Mobile phase | Gradient | Flow Col T | Run time |
|---|---|---|---|---|---|---|
| A | Waters: Acquity ® UPLC ®-DAD and SQD | Waters: BEH C18 (1.7 μm, 2.1 * 50 mm) | A: 10 mM CH$_3$COONH$_4$ in 95% H$_2$O + 5% CH$_3$CN B: CH$_3$CN | From 95% A to 5% A in 1.3 min, held for 0.7 min. | 0.8 55 | 2 |

15 μL of ATP lite (Perkin Elmer) per well and reading on a ViewLux ultraHTS microplate imager (Perkin Elmer). Data was reported as 0050.

In parallel, a similar dilution series of compound was used (200 nL of compound in 100% DMSO) with 40 μL per well of cells transfected with NFκB-luc reporter construct alone ($1.25 \times 10^5$ cells/mL). Six hours after incubation at 37° C., 5% $CO_2$, the luciferase activity was determined by adding 15 μL of Steady Lite Plus substrate (Perkin Elmer) to each well and readout performed on a ViewLux ultraHTS microplate imager (Perkin Elmer). Counterscreen data is reported as LEC.

Activation of ISRE Promoter Elements

The potential of compounds to induce IFN-I was also evaluated by measuring the activation of interferon-stimulated responsive elements (ISRE) by conditioned media from PBMC. The ISRE element of sequence GAAACT-GAAACT (SEQ ID NO: 1) is highly responsive to the STAT1-STAT2-IRF9 transcription factor, activated upon binding of IFN-I to their receptor IFNAR (Clontech, PT3372-5W). The plasmid pISRE-Luc from Clontech (ref. 631913) contains 5 copies of this ISRE element, followed by the firefly luciferase ORF. A HEK293 cell line stably transfected with pISRE-Luc (HEK-ISREluc) was established to profile the conditioned PBMC cell culture media.

Briefly, PBMCs were prepared from buffy coats of at least two donors using a standard Ficoll centrifugation protocol. Isolated PBMCs were resuspended in RPMI medium supplemented with 10% human AB serum and $2 \times 10^5$ cells/well were dispensed into 384-well plates containing compounds (70 μL total volume). After overnight incubation, 10 μL of supernatant was transferred to 384-well plates containing $5 \times 10^3$ HEK-ISREluc cells/well in 30 μL (plated the day before). Following 24 hours of incubation, activation of the ISRE elements was measured by assaying luciferase activity using 40 μL/well Steady Lite Plus substrate (Perkin Elmer) and measured with ViewLux ultraHTS microplate imager (Perkin Elmer). The stimulating activity of each compound on the HEK-ISREluc cells was reported as LEC value, defined as the compound concentration applied to the PBMCs resulting in a luciferase activity at least two fold above the standard deviation of the assay. The LEC in turn indicates the degree of ISRE activation on transfer of a defined amount of PBMC culture medium. Recombinant interferon α-2a (Roferon-A) was used as a standard control compound.

TABLE 2

Activity of compounds of formula (I).
All compounds demonstrated a $CC_{50} > 24$ μM.

| # | Human TLR 7 (LEC) μM | Human TLR 8 (LEC) μM | HEK-ISRE luc (LEC) μM |
|---|---|---|---|
| 1 | 0.6 | >25 | 0.4 |
| 2 | 2.7 | >25 | 0.5 |
| 3 | 0.1 | >25 | 0.03 |
| 4 | 1.4 | >25 | 0.6 |
| 5 | 0.4 | >25 | 0.1 |
| 6 | 3.9 | >25 | 2 |
| 7 | 0.08 | >25 | 0.03 |
| 8 | 0.03 | >25 | 0.01 |
| 9 | 0.07 | >25 | NA |
| 10 | 0.5 | >25 | NA |
| 11 | 0.6 | >25 | NA |

NA = not available

The invention claimed is:

1. A compound of formula (I):

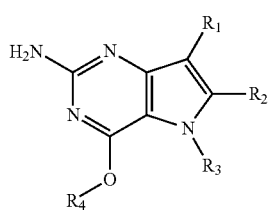

or a pharmaceutically acceptable salt thereof,
wherein
$R_1$ is H;
$R_2$ is H;
$R_3$ is $C_{1-6}$ alkyl substituted by one or more $C_{1-6}$ alkoxy substituents;
or $R_3$ is an alkylaryl optionally substituted by one or more substituents independently selected from the group consisting of halogen, aryloxy, aryl, alkylamino, dialkylamino, $C_{1-6}$ alkyl, —$CO_2H$, —$CO_2C_{1-6}$ alkyl, —$CO_2NH_2$, —$SO_2NH_2$, —CN, and $C_{1-6}$ alkoxy; and
$R_4$ is an alkylaryl substituted by one or more substituents independently selected from the group consisting of halogen, aryloxy, aryl, alkylamino, dialkylamino, $C_{1-6}$ alkyl, —$CO_2H$, —$CO_2C_{1-6}$ alkyl, —$CO_2NH_2$, —$SO_2NH_2$, —CN, and $C_{1-6}$ alkoxy.

2. The compound of claim 1, wherein $R_3$ is a $CH_2$-aryl group optionally substituted by one or more substituents independently selected from the group consisting of halogen, aryloxy, aryl, alkylamino, dialkylamino, $C_{1-6}$ alkyl, —$CO_2H$, —$CO_2C_{1-6}$alkyl, —$CO_2NH_2$, —$SO_2NH_2$, —CN, and $C_{1-6}$ alkoxy.

3. The compound of claim 1, wherein $R_4$ is a $CH_2$-aryl group substituted by one or more substituents independently selected from the group consisting of halogen, aryloxy, aryl, alkylamino, dialkylamino, $C_{1-6}$ alkyl, —$CO_2H$, —$CO_2C_{1-6}$alkyl, —$CO_2NH_2$, —$SO_2NH_2$, —CN, and $C_{1-6}$ alkoxy.

4. The compound of claim 1, wherein $R_3$ is selected from the group consisting of:

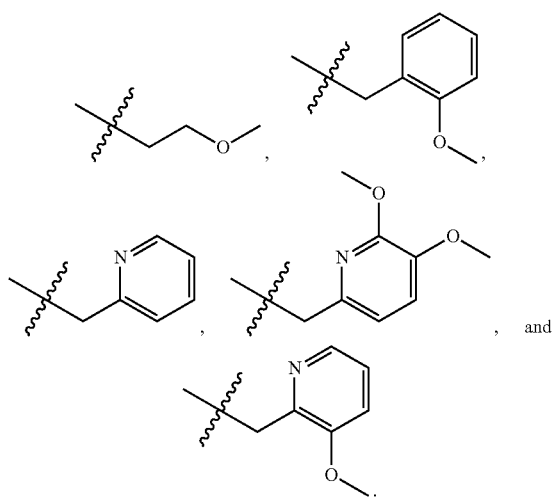

5. The compound of claim 1, wherein $R_4$ is selected from the group consisting of:

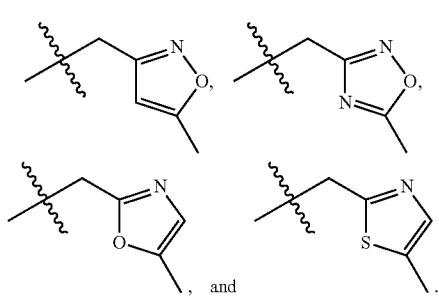

6. The compound of claim 1, wherein:
$R_3$ is

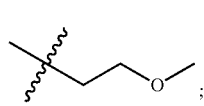 [SMILES: *CCOC]

and
$R_4$ is

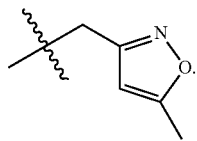 [SMILES: *Cc1cc(C)on1]

7. The compound of claim 1, wherein:

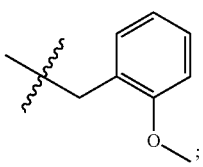 [SMILES: *Cc1ccccc1OC]

and
$R_4$ is

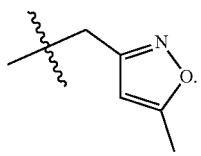 [SMILES: *Cc1cc(C)on1]

8. The compound of claim 1, wherein:
$R_3$ is

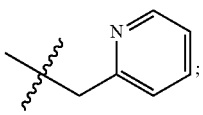 [SMILES: *Cc1ccccn1]

and
$R_4$ is

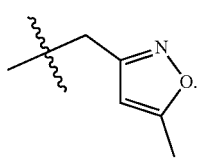 [SMILES: *Cc1cc(C)on1]

9. The compound of claim 1, wherein:
$R_3$ is

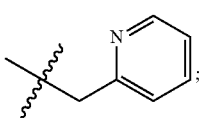 [SMILES: *Cc1ccccn1]

and
R₄ is
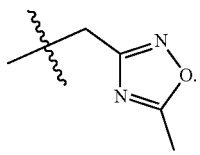 [SMILES: *Cc1noc(C)n1]
10. The compound of claim 1, wherein:
R₃ is
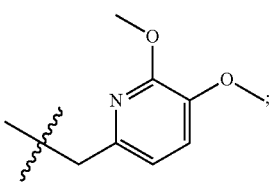 [SMILES: *Cc1ccc(OC)c(OC)n1]
and
R₄ is
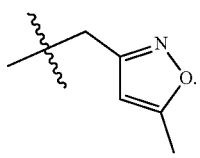 [SMILES: *Cc1cc(C)on1]
11. The compound of claim 1, wherein:
R₃ is
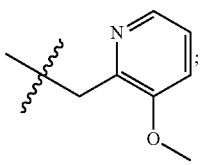 [SMILES: *Cc1ncccc1OC]
and
R₄ is
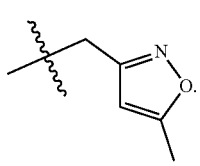
12. The compound of claim 1, wherein:
R₃ is
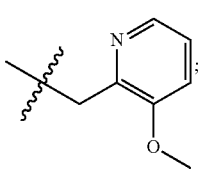 [SMILES: *Cc1ncccc1OC]
and
R₄ is
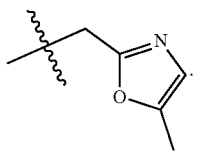 [SMILES: *Cc1ncc(C)o1]
13. The compound of claim 1, wherein:
R₃ is
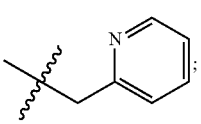 [SMILES: *Cc1ccccn1]
and
R₄ is
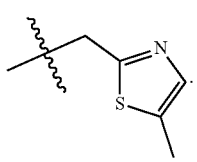 [SMILES: *Cc1ncc(C)s1]
14. The compound of claim 1, wherein:
R₃ is
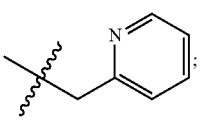 [SMILES: *Cc1ccccn1]
and
R₄ is
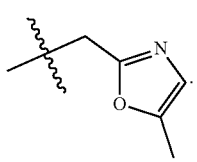 [SMILES: *Cc1ncc(C)o1]
15. The compound of claim 1, selected from the group consisting of:
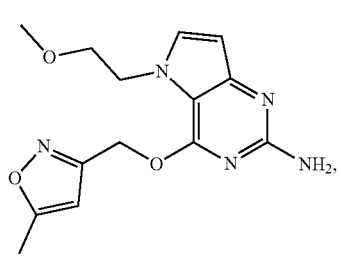

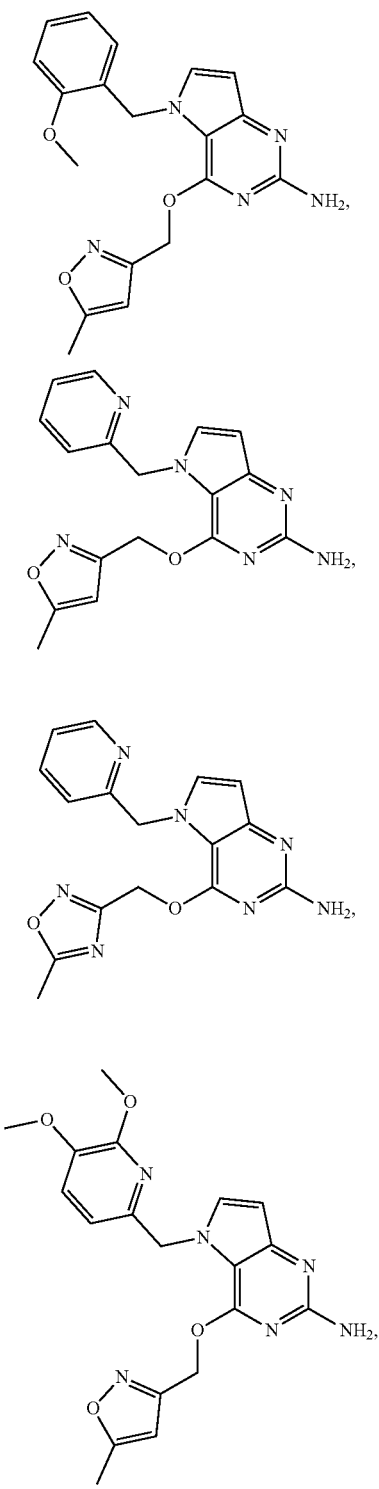

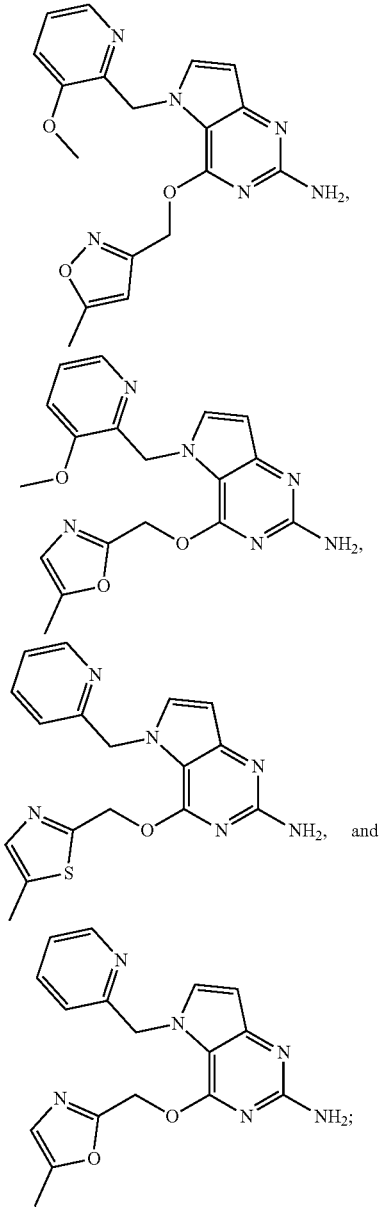

or a pharmaceutically acceptable salt thereof.

16. A pharmaceutical composition comprising a compound of claim 1, or a pharmaceutically acceptable salt thereof, together with one or more pharmaceutically acceptable excipients, diluents or carriers.

17. A method of treating a viral infection in which the modulation of TLR7 is involved in a subject in need thereof, the method comprising administering to the subject a therapeutically effective amount of a compound of claim 1, or a pharmaceutically acceptable salt thereof.

* * * * *

SEQUENCE LISTING

```
<160> NUMBER OF SEQ ID NOS: 1

<210> SEQ ID NO 1
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gaaactgaaa ct                                                         12
```